US012685876B2

(12) United States Patent
Santana Blank et al.

(10) Patent No.: US 12,685,876 B2
(45) Date of Patent: Jul. 21, 2026

(54) DEVICE AND METHOD FOR NON-INVASIVE LIGHT DELIVERY TO A SUBJECT

(71) Applicant: POLYTONE LASER INC., Montreal (CA)

(72) Inventors: Luis Alberto Santana Blank, Montreal (CA); Elizabeth Rodriguez De Santana, Montreal (CA)

(73) Assignee: POLYTONE LASER INC. / LASER POLYTONIE INC., Montreal (CA)

( * ) Notice: Subject to any disclaimer, the term of this patent is extended or adjusted under 35 U.S.C. 154(b) by 289 days.

(21) Appl. No.: 18/449,083

(22) Filed: Aug. 14, 2023

(65) Prior Publication Data

US 2024/0075313 A1 Mar. 7, 2024

Related U.S. Application Data

(60) Provisional application No. 63/450,215, filed on Mar. 6, 2023, provisional application No. 63/403,925, filed on Sep. 6, 2022.

(51) Int. Cl.
*A61N 5/06* (2006.01)
*A61N 5/067* (2006.01)

(52) U.S. Cl.
CPC ........... *A61N 5/0616* (2013.01); *A61N 5/067* (2021.08); *A61N 2005/0626* (2013.01);
(Continued)

(58) Field of Classification Search
CPC .................. A61N 5/0616; A61N 5/067; A61N 2005/0626; A61N 2005/063;
(Continued)

(56) References Cited

U.S. PATENT DOCUMENTS

2005/0177093 A1* 8/2005 Barry ................... A61N 5/0616
604/20
2006/0129211 A1* 6/2006 Canitano .............. A61N 5/0616
607/89
(Continued)

OTHER PUBLICATIONS

International Search Report and Written Opinion issued by the World Intellectual Property Organization (WIPO) on Oct. 26, 2023 in connection with International Application No. PCT/CA2023/051076, 9 pages.
(Continued)

*Primary Examiner* — Benjamin J Klein
*Assistant Examiner* — Alisha J Sircar
(74) *Attorney, Agent, or Firm* — BCF LLP

(57) ABSTRACT

A device for non-invasive light delivery to a subject. The device includes a controller disposed in the housing, the controller being electrically connected to the power source; at least one waveform electronics assembly; a plurality of laser diodes disposed in the housing, the plurality of laser diodes being configured to operate in a super-pulsed regime, the controller being configured to operate the plurality of laser diodes with a Megahertz (MHz) modulation and peak power in milliwatts (mW), the plurality of laser diodes including at least one near-infrared laser diode, at least one mid-infrared laser diode, at least one far-infrared laser diode, and at least one visible-range laser diode; a plurality of optical fibers bundled into at least one fiber bundle, a distal end of the at least one fiber bundle being arranged and configured for delivering light from the plurality of optical fibers to the subject.

19 Claims, 5 Drawing Sheets

(52) U.S. Cl.
  CPC .................. *A61N 2005/063* (2013.01); *A61N 2005/0651* (2013.01); *A61N 2005/066* (2013.01); *A61N 2005/0663* (2013.01)

(58) Field of Classification Search
  CPC ...... A61N 2005/0651; A61N 2005/066; A61N 2005/0663; A61N 5/0613; A61N 2005/0659; A61N 2005/0662; A61B 2017/00154
  See application file for complete search history.

(56) References Cited

U.S. PATENT DOCUMENTS

| | | | | |
|---|---|---|---|---|
| 2007/0239232 A1* | 10/2007 | Kurtz | .................... | G02B 6/001 |
| | | | | 607/87 |
| 2014/0128941 A1* | 5/2014 | Williams | .............. | H05B 45/00 |
| | | | | 315/193 |
| 2019/0083809 A1* | 3/2019 | Zhang | ................. | A61N 5/0616 |
| 2020/0384287 A1 | 12/2020 | Hetz | | |

OTHER PUBLICATIONS

Santana-Blank, Luis et al., "Quantum Leap" in Photobiomodulation Therapy Ushers in a New Generation of Light-Based Treatments for Cancer and Other Complex Diseases: Perspective and Mini-Review, Photomedicine and Laser Surgery, 2016, pp. 93-101, vol. 34, No. 3.

Santana-Blank, Luis et al., Water-light interaction: A novel pathway for multi hallmark therapy in cancer, International Journal of Cancer Therapy and Oncology, published online Dec. 21, 2013.

Muste, Justin C. et al., Photobiomodulation therapy in age-related macular degeneration, Current Opinion of Ophthalmology, 2021, pp. 225-232, vol. 32.

Muste, Justin C. et al., Photobiomodulation Therapy for Age-Related Macular Degeneration and Diabetic Retinopathy: A Review, Clinical Ophthalmology, 2021, pp. 3709-3720, vol. 15.

Santana-Blank, Luis et al., Photo-Infrared Pulsed Bio-Modulation (PIPBM): A Novel Mechanism for the Enhancement of Physiologically Reparative Responses, Photomedicine and Laser Surgery, 2005, pp. 416-424, vol. 23, No. 4.

Santana-Blank, Luis et al., Photobiomodulation of Aqueous Interfaces as Selective Rechargeable Bio-Batteries in Complex Diseases: Personal View, Photomedicine and Laser Surgery, 2012, pp. 242-249, vol. 30, No. 5.

Santana-Blank, Luis et al., Short-Term Bioeffects of an Infrared Pulsed Laser Device on Burned Rat Skin Monitored by Transverse Relaxation Times (NMR), Lasers in Surgery and Medicine, 2000, pp. 411-419, vol. 27.

Rodriguez-Santana, Elizabeth et al., H-NMR Spin-Lattice and Correlation Times of Burned Soft-Tissue After Treatment with an Infrared Pulsed Laser Device, Lasers in Surgery and Medicine, 2003, vol. 33.

Santana-Blank, Luis et al., Phase I Trial of an Infrared Pulsed Laser Device in Patients with Advanced Neoplasias, Clinical Cancer Research, 2002, pp. 3082-3091, vol. 8.

Santana-Blank, Luis et al., Microdensitometry of T2-Weighted Magnetic Resonance (MR) Images From Patients With Advanced Neoplasias in a Phase I Clinical Trial of an Infrared Pulsed Laser Device (IPLD), Lasers in Surgery and Medicine, 2004, pp. 398-406, vol. 34.

Santana-Blank, Luis et al., Photo-Induced Cytomorphologic Changes in an Advanced Cancer Phase I Clinical Trial, Lasers in Surgery and Medicine, 2002, pp. 18-25, vol. 30.

Santana-Blank, Luis et al., Evaluation of serum levels of tumour necrosis factor-alpha (TNF-x) and soluble IL-2 receptor (sIL-2R) and CD4, CD8 and natural killer (NK) populations during infrared pulsed laser device (IPLD) treatment, Clinical and Experimental Immunology, 1992, pp. 43-48, vol. 90.

Tata, Darrell B. et al., Near-IR induced suppression of metabolic activity in aggressive cancers, Mechanisms for Low-Light Therapy II, Feb. 21, 2007.

Tata, Darrell B. et al., Near-IR Picosecond Pulsed Laser Induced Suppression of Metabolic Activity in Malignant Human Brain Cancer: An In-Vitro Study, Proceedings of Light-Activated Tissue Regeneration and Therapy Conference, Lecture Notes in Electrical Engineering, 2008, pp. 11 to 19, vol. 12.

Schlichting, Abby et al., In-vitro suppression of metabolic activity in malignant human glioblastomas due to pulsed low frequency electric potential exposures, Mechanisms for Low-Light Therapy V, Feb. 25, 2010.

Hamblin, Michael R. et al., Photobiomodulation and Cancer: What Is the Truth?, Photomedicine and Laser Surgery, 2018, pp. 241-245, vol. 36, No. 5.

Rodriguez-Santana, Elizabeth et al., Photo-infrared pulsed biomodulation in age-related macular degeneration associated to neurological disease: one interventional case report and mini-review, Journal of Chinese Clinical Medicine, 2008, pp. 470-477, vol. 3, No. 8.

Rodriguez-Santana, Elizabeth et al., Hypotensor bioeffect of laser photobiomodulation over intraocular pressure: Noncomparative interventional case review, Journal of Chinese Clinical Medicine, 2011, pp. 1-13, vol. 6, No. 4.

* cited by examiner

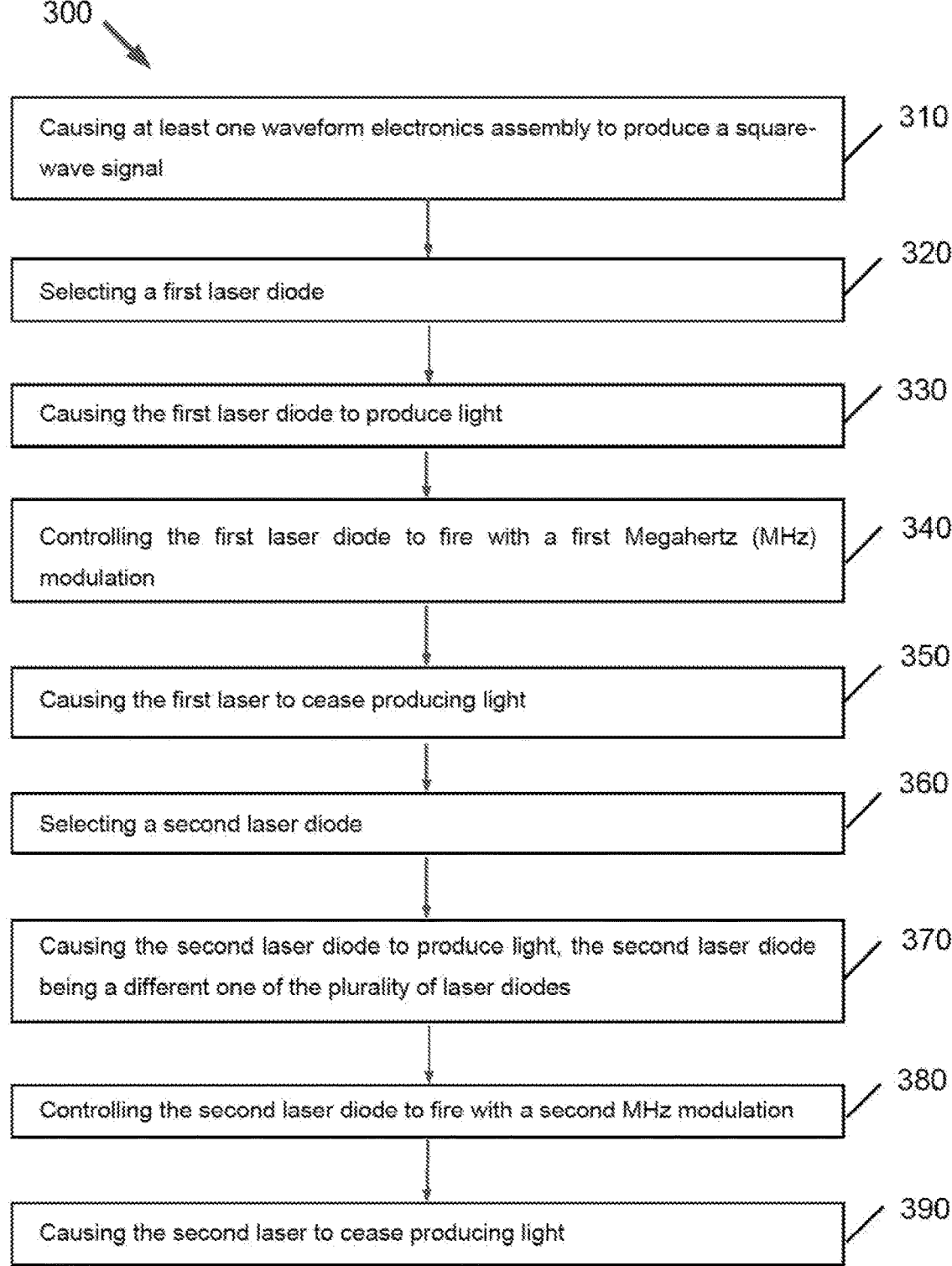

300

Causing at least one waveform electronics assembly to produce a square-wave signal    310

Selecting a first laser diode    320

Causing the first laser diode to produce light    330

Controlling the first laser diode to fire with a first Megahertz (MHz) modulation    340

Causing the first laser to cease producing light    350

Selecting a second laser diode    360

Causing the second laser diode to produce light, the second laser diode being a different one of the plurality of laser diodes    370

Controlling the second laser diode to fire with a second MHz modulation    380

Causing the second laser to cease producing light    390

FIGURE 5

DEVICE AND METHOD FOR NON-INVASIVE LIGHT DELIVERY TO A SUBJECT

CROSS-REFERENCE

The present application claims priority to U.S. Provisional Patent Application No. 63/403,925, entitled "Device and Method for Non-Invasive Light Delivery to a Subject," filed Sep. 6, 2022, and U.S. Provisional Patent Application No. 63/450,215, entitled "Non-Invasive, Dynamic, Multi-Wavelength, Multi-Node Photobiomodulation Therapy Methods and Systems for Treatment of Complex Diseases," filed Mar. 6, 2023, the entirety of both of which is incorporated by reference herein.

FIELD

The present technology relates to devices and methods for non-invasive light delivery to a subject.

BACKGROUND

For treatment of various conditions, different devices have been proposed for delivering non-ionizing electromagnetic (EM) signals to a subject, the process being referred to in some cases as photobiomodulation (PBM) therapy. The terms Low-Level Laser Therapy (LLLT) and laser biostimulation are also sometimes used to describe the procedures provided in cooperation with such devices.

To avoid non-specific toxicity, the non-surgical treatment of complex disease (CDs) generally relies on agents targeting single molecular targets. However, diseased tissues can often adapt to variations in one molecular pathway, leading to partial or transitory responses followed by progression or relapse.

In PBM therapy, devices generally operate within a certain target-related wavelength range. However, the coupling of signal and receptor characteristics, which determine biological outcome, can be optimal for only one set of conditions.

Devices constructed therefore may then be limited to a certain subset of conditions, and each different treatment regime may require its own device. As diseased tissue adapts, a particular device may no longer be adequate for treating a given subject. This can be costly and cumbersome for operators providing PBM therapy to subjects having a broad range of conditions to be addressed.

There is thus a desire to provide a device that addresses at least some of these disadvantages.

SUMMARY

Embodiments of the present technology have been developed based on developers' appreciation of shortcomings associated with the prior art.

In one aspect, various embodiments of the present technology provide a device capable of providing non-invasive light delivery to a subject in a variety of wavelengths. The device as described herein includes a plurality of lasers in different wavelength ranges, modulated at different ranges of high frequency (on the order of megahertz) and with different ranges of peak power (on the order of milliwatts), as well as an internal controller capable of selectively activating and deactivating each laser in order to provide various light-delivery patterns to the subject. In at least some embodiments, multiple sets of the plurality of lasers may be included, such that fiber bundles extending from each set can be arranged on a different portion of the body of the subject to provide light therapy to multiple locations on the subject simultaneously. One or more light therapy programs (referred to herein as a light production program) can be saved to the controller, in order to provide a device pre-programmed for clinic or at home use of the device. In at least some cases, communications with the controller can be limited, such that only an approved operator or programmer may modify the light therapy programs. The device is configured to provide super-pulsed, low power (mW) light delivery to the subject, with each laser being modulating in a Megahertz (MHz) pulse rate, the particular pulse rate being controlled by the controller.

According to one aspect of the present technology, there is provided a device for non-invasive light delivery to a subject. The device including a housing; a power source disposed in the housing; a controller disposed in the housing, the controller being electrically connected to the power source; at least one waveform electronics assembly disposed in the housing, the at least one waveform electronics assembly being operatively connected to the power source and the controller; a plurality of laser diodes disposed in the housing, each of the plurality of laser diodes being operatively connected to the at least one waveform electronics assembly, the plurality of laser diodes being configured to operate in a super-pulsed regime, the controller being configured to operate the plurality of laser diodes with a Megahertz (MHz) modulation, the plurality of laser diodes comprising at least one near-infrared laser diode, at least one mid-infrared laser diode, at least one far-infrared laser diode, and at least one visible-range laser diode; a plurality of optical fibers including at least one first fiber optically connected to the at least one near-infrared laser diode at a proximal end thereof, at least one second fiber optically connected to the at least one mid-infrared laser diode at a proximal end thereof, at least one third fiber optically connected to the at least one far-infrared laser diode at a proximal end thereof, and at least one fourth fiber optically connected to the at least one visible-range laser diode at a proximal end thereof, the plurality of optical fibers being bundled into at least one fiber bundle, the at least one fiber bundle extending from an interior of the housing to an exterior of the housing, a distal end of the at least one fiber bundle being arranged and configured for delivering light from the plurality of optical fibers to the subject, the distal end of the at least one fiber bundle being formed at least in part by a distal end of each of the plurality of optical fibers.

In some embodiments, the controller comprises at least one storage media and at least one processor; and the processor is configured to execute a light production program saved to the storage media.

In some embodiments, the controller is configured to selectively activate each of the plurality of laser diodes according to instructions of the light production program.

In some embodiments, the device further includes a communication assembly operatively connected to the controller, the communication assembly being configured to provide outward communication of information from the controller.

In some embodiments, the communication assembly is further configured to receive inward communication, the controller being selectively re-programmable when selectively connected to a secure communication connection via the communication assembly.

In some embodiments, the at least one waveform electronics assembly includes at least one waveform generator; at least one frequency selector circuit operatively connected to the at least one waveform generator; and at least one buffering circuit operatively connected to the at least one frequency selector circuit.

In some embodiments, the at least one waveform electronics assembly includes a plurality of laser waveform assemblies; each assembly of the plurality of laser waveform assemblies is operatively connected to a corresponding one of the plurality of laser diodes; and each assembly of the plurality of laser waveform assemblies includes a waveform generator, a frequency selector circuit operatively connected to the waveform generator, and a buffering circuit operatively connected to the frequency selector circuit and the corresponding one of the plurality of laser diodes.

In some embodiments, the at least one near-infrared laser diode includes a first near-infrared laser diode configured to operate at a pulse frequency from about 9.5 MHz to about 10 MHz; and a second near-infrared laser diode configured to operate at a pulse frequency from about 3 MHz to about 3.5 MHz.

In some embodiments, the first near-infrared laser diode has an operational wavelength selected from a wavelength range of about 780 nm to about 810 nm.

In some embodiments, the second near-infrared laser diode has an operational wavelength selected from a wavelength range of about 904 nm to about 945 nm.

In some embodiments, the at least one mid-infrared laser diode is configured to operate at a pulse frequency from about 6 MHz to about 6.5 MHz.

In some embodiments, the at least one mid-infrared laser diode has an operational wavelength selected from a wavelength range of about 1200 to about 1550 nm.

In some embodiments, the at least one far-infrared laser diode is configured to operate at a pulse frequency from about 7 MHz to about 7.5 MHz.

In some embodiments, the at least one far-infrared laser diode has an operational wavelength selected from a wavelength range of about 2900 nm to about 3200 nm.

In some embodiments, the at least one visible-range laser diode includes a first visible laser diode configured to operate at a pulse frequency from about 4 MHz to about 4.5 MHz; and a second visible laser diode configured to operate at a pulse frequency from about 5 MHz to about 5.5 MHz.

In some embodiments, the first visible laser diode has an operational wavelength selected from a wavelength range of about 630 nm to 700 nm; and the second visible laser diode has an operational wavelength selected from a wavelength range of about 570 nm to about 600 nm.

In some embodiments, the device further includes at least one adhesive pad connected to the distal end of the at least one fiber bundle; and when the at least one adhesive pad is applied to the subject, the at least one adhesive pad is configured to position the distal end of the at least one fiber bundle such that light from the plurality of laser diodes is delivered to the subject when the device is in use.

In some embodiments, the at least one waveform electronics assembly includes a plurality of waveform electronics assemblies; the plurality of laser diodes includes a plurality of diode groups, each diode group of the plurality of diode groups includes at least: a first near-infrared laser diode, a second near-infrared laser diode, a mid-infrared laser diode, a far-infrared laser diode, a first visible-range laser diode, and a second visible-range laser diode, each diode group being operatively connected to a corresponding one of the plurality of waveform electronics assemblies; the at least one fiber bundle including a plurality of fiber bundles; and each fiber bundle of the plurality of fiber bundles being optically connected to a corresponding one of the plurality of diode groups.

According to another aspect of the present technology, there is provided a method for delivering light to a subject using a device for non-invasive light delivery, the method being executed by a controller of the device, the method including causing at least one waveform electronics assembly to produce a square-wave signal, a plurality of laser diodes of the device being operatively connected to the at least one waveform electronics assembly for receiving the square-wave signal therefrom; selecting a first laser diode from a plurality of laser diodes, the plurality of laser diodes including at least one near-infrared laser diode, at least one mid-infrared laser diode, at least one far-infrared laser diode, and at least one visible-range laser diode; causing the first laser diode to produce light, light from the first laser diode being conducted to the subject by a first fiber of a plurality of optical fibers of the device, controlling the first laser diode to fire with a first Megahertz (MHz) modulation; causing the first laser diode to cease producing light; selecting a second laser diode from a plurality of laser diodes; causing the second laser diode to produce light, the second laser diode being a different one of the plurality of laser diodes from the plurality of laser diodes, light from the second laser diode being conducted to the subject by a second fiber of a plurality of optical fibers; controlling the second laser diode to fire with a second MHz modulation; and causing the second laser to cease producing light.

In some embodiments, causing the first laser diode to produce light includes, in response to selecting the at least one near-infrared laser diode, causing the at least one near-infrared laser diode to operate at one of: a pulse frequency from about 3 MHz to about 3.5 MHz and a pulse frequency of about 9.5 MHz to about 10 MHz; in response to selecting the at least one mid-infrared laser diode, causing the at least one mid-infrared laser diode to operate at a pulse frequency from about 6 MHz to about 6.5 MHz; in response to selecting the at least one far-infrared laser diode, causing the at least one far-infrared laser diode to operate at a pulse frequency from about 7 MHz to about 7.5 MHz; and in response to selecting the at least one visible-range laser diode, causing the at least one visible-range laser diode to operate at one of: a pulse frequency from about 4 MHz to about 4.5 MHz and a pulse frequency from about 5 MHz to about 5.5 MHz.

Quantities or values recited herein are meant to refer to the actual given value. The term "about" is used herein to refer to the approximation to such given value that would reasonably be inferred based on the ordinary skill in the art, including equivalents and approximations due to the experimental and/or measurement conditions for such given value.

Explanations and/or definitions of terms provided in the present application take precedence over explanations and/or definitions of these or similar terms that may be found in any documents incorporated herein by reference.

The functions of the various elements shown in the figures, including any functional block labeled as a "controller", may be provided through the use of dedicated hardware as well as hardware capable of executing software in association with appropriate software. When operation of the controller is provided by a processor, the functions may be provided by a single dedicated processor, by a single shared processor, or by a plurality of individual processors, some of which may be shared. In some embodiments of the present technology, the processor may be a general-purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, application specific integrated circuit (ASIC), field programmable gate array (FPGA), read-only memory (ROM) for storing software, random access memory (RAM), and non-volatile storage. Other hardware, conventional and/or custom, may also be included.

The examples and conditional language recited herein are principally intended to aid the reader in understanding the principles of the present technology and not to limit its scope to such specifically recited examples and conditions. It will be appreciated that those skilled in the art may devise various systems that, although not explicitly described or shown herein, nonetheless embody the principles of the present technology.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 5 is a flowchart depicting a method of operation of the device of claim 1.

It should also be noted that, unless otherwise explicitly specified herein, the drawings are not drawn to scale.

DETAILED DESCRIPTION

Figure 1:
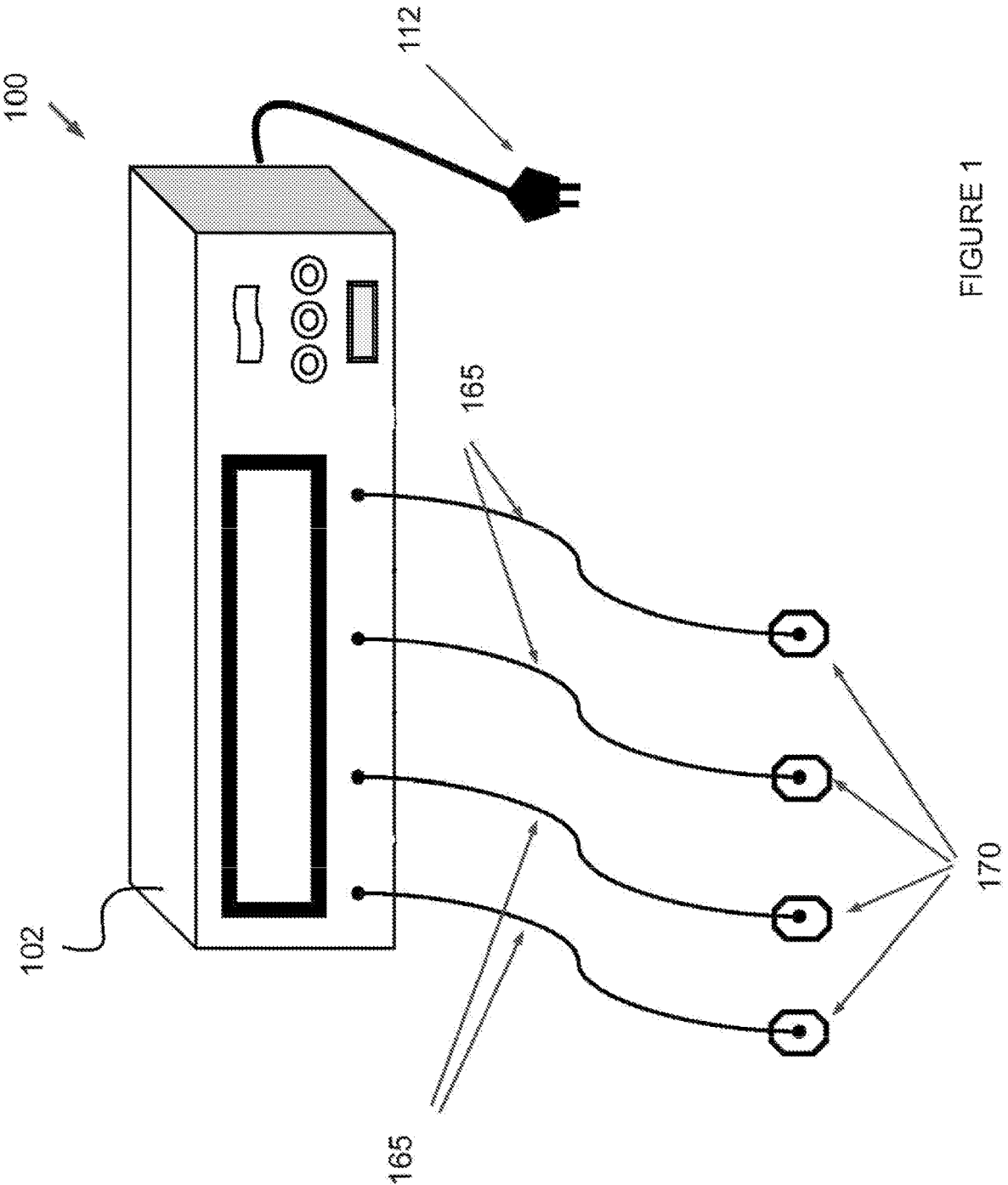
FIG. 1 is a perspective view of a light-delivery device according to non-limiting embodiments of the present technology.
Figure 2:
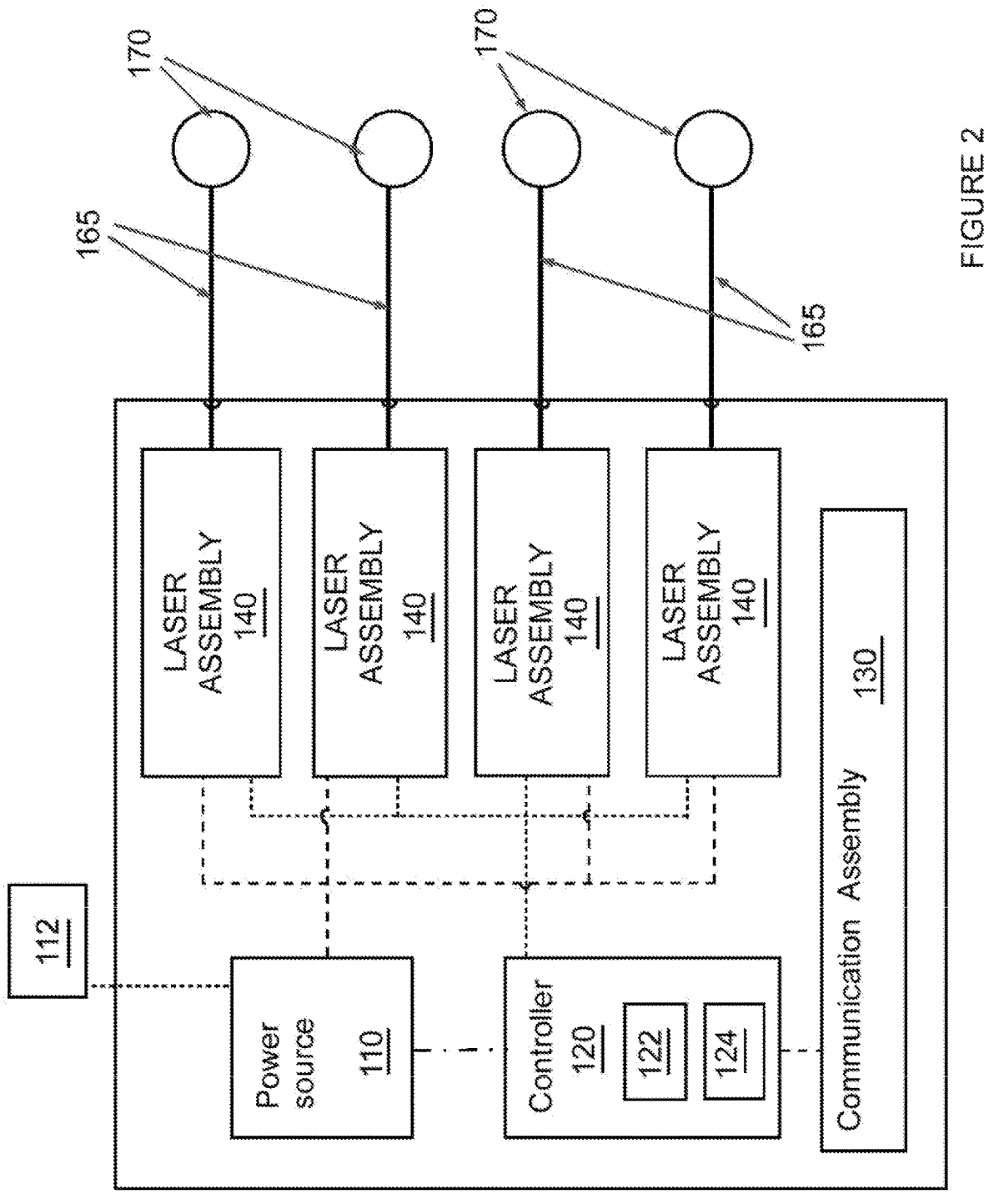
FIG. 2 is a schematic diagram of the device of claim 1.

With reference to FIGS. 1 and 2, one non-limiting embodiment of a device 100 for providing non-invasive light delivery to a subject is illustrated. While the subject as generally described herein is a human subject receiving a non-invasive (i.e. applied to the skin), non-thermal (i.e. temperature increases <0.01° C.), and non-ionizing light treatment, it is contemplated that animals, including other mammals, could be a light-receiving subject in non-limiting cases.

The device 100 includes a housing 102 for enclosing and protecting components of the device 100 therein. The shape and aesthetic form of the housing 102 as illustrated is not meant to be limiting, and a variety of forms are contemplated. In at least some embodiments, the housing 102 is arranged to be selectively openable in order to provide access to an operator or programmer of the device 100, for example for maintenance, repair, or adjustment (such as reprogramming) of the device 100. In at least some embodiments, it is also contemplated that the housing 102 could be secured in the closed position, impeding access to the internal components by an end user or the subject, in order to aid in preventing interference with the internal components. In some such cases, the housing 102 could be provided with securing means, including for example a locking mechanism, in order to allow selective access to the operator or programmer while also impeding access by the end user or the subject. In at least some embodiments, the housing 102 could further include arrangements for cooling components disposed therein, including but not limited to: ventilation holes or slots, fans, and cooling systems.

The device 100 includes a power source 110 disposed in the housing 102. The power source 110 provides electrical power to a plurality of components of the device 100, according to the required electrical input of the various components. The particular technology of the power source 110 is not meant to be particularly limited. Depending on the embodiment, the power source 110 could include various electronic components, including for example transformers for outputting electric power in different voltage or current configurations adapted to the components powered thereby. The power source 110 includes an electrical plug 112 for operatively connecting the device 100 to a standard electrical outlet for providing an electricity source to the power source 110. In at least some embodiments, the device 100 could additionally or alternatively include a rechargeable battery.

The device 100 includes a controller 120 disposed in the housing 102 and powered by the power source 110. Broadly, the controller 120 manages operation of components of the device 100, as will be described further below. The controller 120 may be implemented in a variety of forms; arrangement of a computer-implemented assembly to form the controller 120 to manage operation of the components described herein are generally assumed to be within the capabilities of persons of skill in the art and therefore will not be described herein in more detail. Generally, the controller 120 includes one or more storage media 122 and one or more processors 124. The processor 124 is configured to execute a light production program (described further below), the program being saved to the storage media 122.

The device 100 further includes a communication assembly 130 operatively connected to the controller 120 and the power source 110. The communication assembly 130 is configured to provide at least outward communication of information from the controller 120. For example, the communication assembly 130 could be configured to send confirmation, such as dates and time duration, of use of the device 100 by the subject to a remotely located operator.

While not particularly limited in the present context, the communication assembly 130 includes a WiFi router/modem (not shown) communicably connected to the controller 120 for transmitting information therefrom and transferring received information thereto. Depending on the embodiment, it is contemplated that the communication assembly 130 could include various additional or alternative communication components, including but not limited to: a communication bus, Bluetooth™ modules, and hard-wired ethernet connection modules. Notwithstanding the particular choice of communication regime, the communication assembly 130 generally operates under a secure communication method, such that control of the device 100 is limited to approved parties (such as the operator or programmer). In some embodiments, incoming communication could be limited or blocked to prevent alteration of the light production program stored to the controller 120.

In at least some embodiments, the communication assembly 130 could be further configured to receive inward communication, the controller being selectively re-programmable when selectively connected to a secure communication connection via the communication assembly 130. In some arrangements, the device 100 could be deactivated by a remotely-location operator in order to impede misuse by the end user.

In order to produce light for the light production program, the device 100 includes a plurality of laser assemblies 140. While four laser assemblies 140 are illustrated in the present example, it is contemplated that the device 100 could have more or fewer assemblies 140, including as few as one assembly 140. The laser assemblies 140 are described in greater detail below.

The device 100 includes a plurality of fiber bundles 165 to propagate light produced by the laser assemblies 140 to the subject. Each fiber bundle 165 extends from and is operatively connected to a corresponding one of the laser assemblies 140. Specifically, a proximal end of each fiber bundle 165 is connected to a corresponding one of the laser assemblies 140. Each fiber bundle 165 extends from an interior of the housing 102 to an exterior of the housing 102. As will be described in more detail below, each fiber bundle 165 is formed from a plurality of optical fibers 160 operatively connected to the corresponding laser assembly 140.

A distal end of each fiber bundle 165 is arranged and configured for delivering light from the optical fibers 160 to the subject, the distal end of the fiber bundle 165 being formed at least in part by a distal end of each of the optical fibers 160. In the illustrated embodiment, the distal end of each fiber bundle 165 includes an adhesive pad 170 connected thereto. When the device 100 is in use, the adhesive pad 170 is applied to the subject at a position to deliver light according to the light production program. For devices 100 with multiple fiber bundles 165 and adhesive pads 170 (such as the illustrated example), the adhesive pads 170 may be connected to a same subject at different locations of the body, in order to deliver light to different parts of the body simultaneously.

Specifically, the adhesive pads 170 are configured to position the distal end of the fiber bundle 165 such that light from laser diodes (described below) of the laser assembly 140 is delivered to the subject. By adhering the distal end of the fiber bundle 165 to the subject, the adhesive pads 170 further aid in maintaining the positioning of the fiber bundle distal end in order to properly deliver light to the subject even under movement of the subject (for example), in at least some cases improving comfort of the subject while using the device 100.

Depending on the embodiment, different means could be used with or included with the device 100 for retaining the positioning and/or connection of each fiber bundle 165 to the subject. Additionally or alternatively to the adhesive pads 170, the connecting or application means could include but are not limited to: cuffs, tape, straps, belts, bracelets, and necklaces. While not illustrated herein, it is contemplated that the fiber bundle 165 and/or the adhesive pads 170 (or other connection means) could include one or more optical elements to shape or condition light delivered from the fiber bundle 165.

Figure 3:
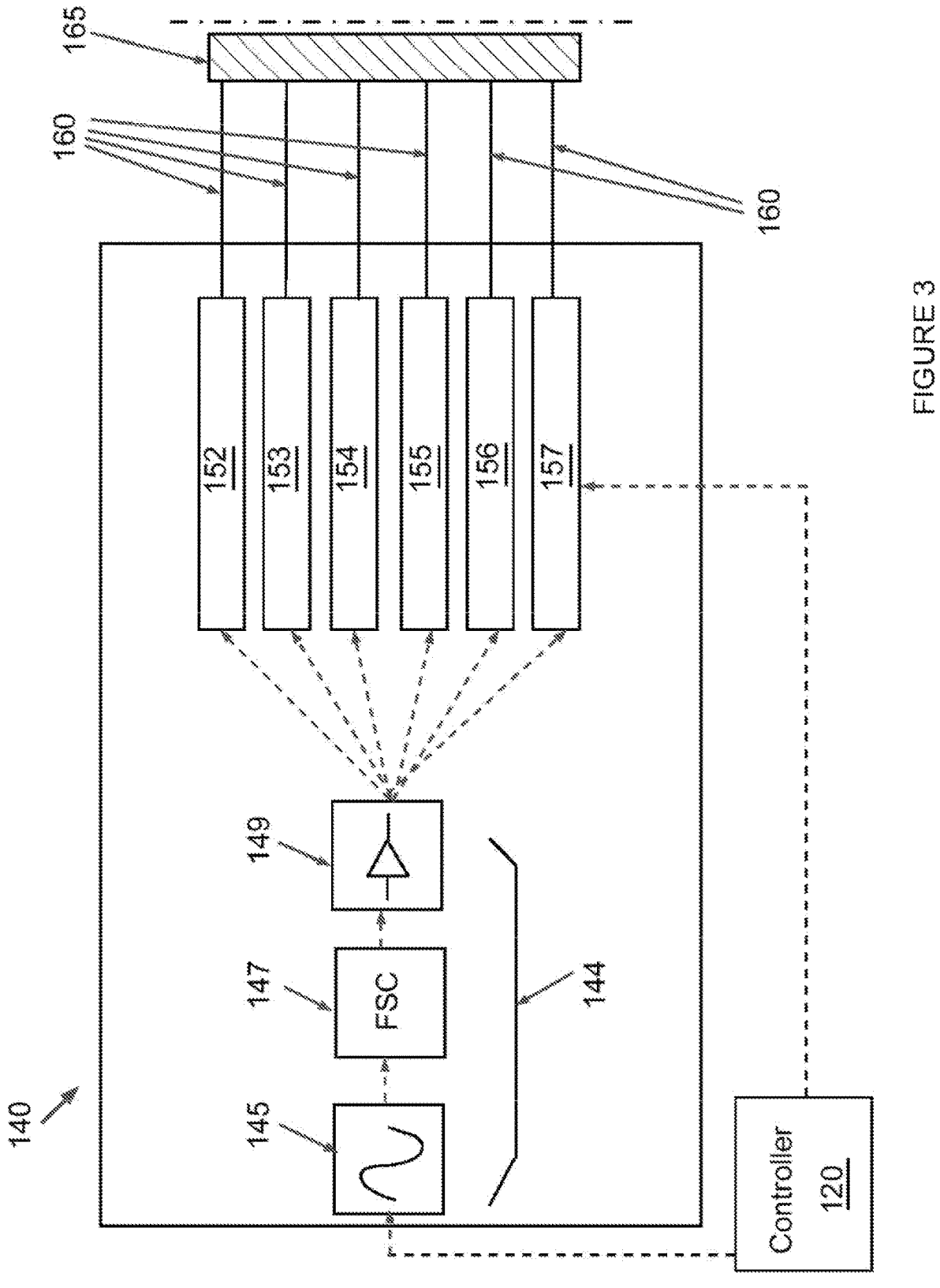
FIG. 3 is a schematic diagram of a laser assembly of the device of FIG. 1.

One laser assembly 140 of the device 100 is illustrated in isolation and in more detail in FIG. 3. Each laser assembly 140 is generally identical within a given device 100, and thus only one of the assemblies 140 will be described herein. It is contemplated that in at least some embodiments of the device 100, differences could exist between different laser assemblies 140 thereof. While each laser assembly 140 is illustrated as one packaged module, this is simply for ease of illustration; there is no specific packaging or separation between different laser assemblies 140 within the housing 102 contemplated. Depending on the embodiment, there could be structures, such as baffles or beam blockers for example, included in the housing 102 in order to limit cross-talk or noise within the housing 102.

The laser assembly 140 includes a waveform electronics assembly 144 disposed in the housing 102. The waveform electronics assembly 144 is operatively connected to the power source 110 and the controller 120. Components and use of the waveform electronics assembly 144 are described further below.

The laser assembly 140 also includes a plurality of laser diodes 152, 153, 154, 155, 156, 157 (referred to herein as the diodes 152-157) disposed in the housing 102. Each laser diode 152-157 is individually and operatively connected to the waveform electronics assembly 144 and the controller 120.

By the present technology, the laser diodes 152-157 are configured to operate in a super-pulsed regime, where the diodes 152-157 are operated to output ("fire") with a relatively high pulse rate and a relatively low power output. Specifically, the controller 120 is configured to operate the laser diodes 152-157 with a Megahertz (MHz) pulse modulation. The MHz modulation of each laser diode 152-157 is specific to a given diode 152-157 and is set out below. On average in the super-pulsed regime, each laser diode 152-157 produces output pulses with a power in the range of milliwatts (mW) with a duty cycle of generally less than 50%.

The term "super-pulsed regime" refers to a mode of laser operation commonly used in the field of photobiomodulation. Super-pulsed operation regimes are generally designed to operate a laser to output a pulsed signal with a peak power in watts (W), a pulse frequency in a kilohertz (kHz) range, and a pulse duration in nanoseconds (e.g. 200 ns). For example, such lasers under super-pulsed regime operation are used in the treatment of wound healing, musculoskeletal pain and inflammation. It is noted that such super-pulsed regimes may be designed to operate outside the electronic parameters established by the manufacturer of a given laser under operation, for example laser diodes having a peak power in Watts (e.g. 10-200 W) and a pulse frequency <10 kilohertz (KHz). By altering the signal to mW and MHz respectively, the laser may be rendered electronically inefficient. For the biological applications sought for at least some embodiments of the present device 100, such signals are efficient from the biological perspective. Such modified signals preserve a non-thermal effect while achieving greater penetration since the pulses in MHz reduce impedance in tissues. See, U.S. Pat. No. 5,231,984 to Lasb Laser Corp., issued Aug. 3, 1993, the entirety of which is incorporated herein by reference.

Components of the waveform electronics assembly 144 will now be described in more detail. The assembly 144 includes a waveform generator 145 operably connected to the controller 120. In the present embodiment, the waveform generator 145 (also referred to as a signal generator) is specifically an oscillator 145. In other embodiments, other types of signal generators could be implemented in place of the oscillator 145. The oscillator 145 provides the pulse shape and duty cycle for each laser diode 152-157 when the device 100 is in operation. By the present technology, a square-wave form is generally used to provide an on-off state light illumination, where the light is delivered at a given power or is turned off, but not ramping between those states. In at least some embodiments, the oscillator 145 could be configured to output a sinusoidal or sawtooth waveform.

The waveform electronics assembly 144 also includes a frequency selector circuit (FSC) 147 operatively connected to the oscillator 145. The FSC 147 acts to modulate the signal voltage of the signal received from the oscillator 145. Specifically, the FSC 147 modulates the signal to reduce amplitude of the signal, from the order of watts to the order of milliwatts, while simultaneously increasing the signal frequency, from the order of kilohertz to the order of megahertz. Specific components of the frequency selector circuit 147 may vary, and various configurations of the circuit 147 are envisioned.

The FSC 147 is further operably connected to the controller 120 for receiving instructions therefrom. Specifically, the FSC 147 controls transmission of signals from the oscillator 145 to the laser diodes 152-157, in order to manage the frequency and power of light production ("firing") of the laser diodes 152-157 according to the light production program. In some embodiments, it is contemplated that the device 100 could include a plurality of FSCs 147, one for each laser diode 152-157, in order to provide a separate control circuit for each laser diode 152-157.

The waveform electronics assembly 144 also includes a buffering circuit 149 operatively connected to the FSC 147. The buffering circuit 149 provides a signal buffer for the waveform signals before delivery thereof to the laser diodes 152-157 in order to prevent current spikes to aid in limiting possible damage to the diodes 152-157.

Depending on the embodiment, it is contemplated that the waveform electronics assembly 144 could include alternative or additional components. For example, in some embodiments the waveform electronics assembly 144 could include additional transistors, capacitors, etc. in order to manage signal production and laser diode operation. It is also contemplated that additional electronic components could be included between the waveform electronics assembly 144 and the laser diodes 152-157.

As is mentioned briefly above, the fiber bundle 165 of each laser assembly 140 is formed from a plurality of optical fibers 160. Each optical fiber 160 is operatively connected to a corresponding one of the laser diodes 152-157, with a proximal end of each fiber 160 receiving light from its corresponding diode 152-157. Depending on the particular embodiment of the device 100 and/or depending on a particular model of laser diode 152-157, it is contemplated that any number of filters, apertures, and optical elements could be included. For instance, for IR laser diodes 152-155 (described below), an ultraviolet (UV) blocking filter could be included to prevent UV light from some types of IR laser diodes from being transmitted into the corresponding fibers 160.

The distal ends of the fibers 160 then form the distal end of the fiber bundle 165. In at least some embodiments, a sleeve or flexible tube could be disposed around the fibers 160 in order to form the fiber bundle 165 and protect the fibers 160 therein. It is also contemplated that a light-blocking sleeve could surround the fiber bundle 165 to prevent stray light from scattering from the fiber bundle 165 and/or infiltration of ambient light into the fiber bundle 165.

Figure 4:
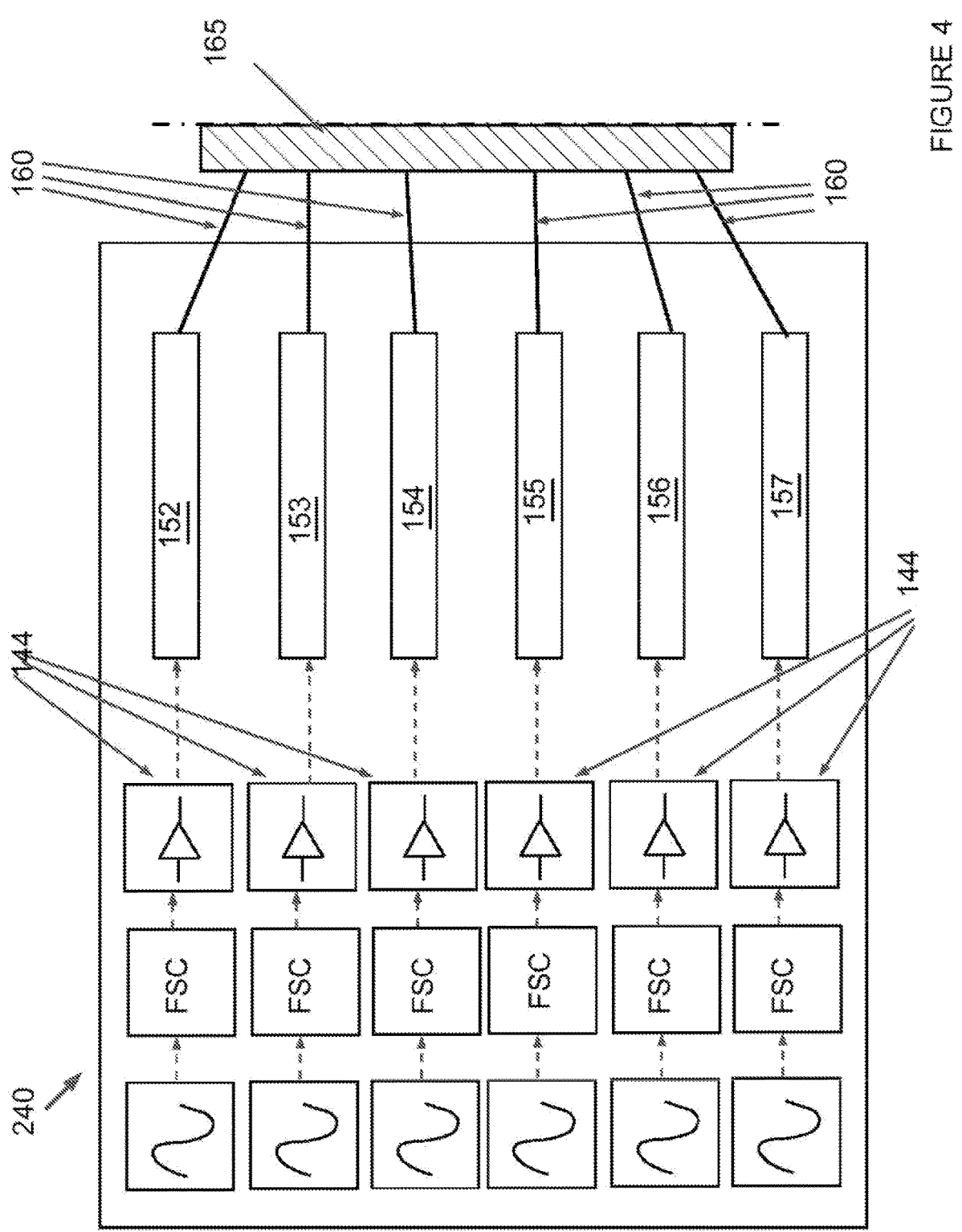
FIG. 4 is a schematic diagram of another non-limiting embodiment of a laser assembly for the device of FIG. 1.

As is illustrated in FIG. 4, a laser assembly 240 of another non-limiting embodiment of the device 100 includes a plurality of waveform electronics assemblies 144. Specifically, the laser assembly 240 includes one waveform electronics assembly 144 for each laser diode 152-157.

Returning to FIG. 3, specifics of each laser of the laser diodes 152-157 will be described in more detail. In at least some embodiments, the laser assembly 140 could include additional laser diodes in addition to the diodes described hereafter.

Each laser assembly 140 includes one or more near-infrared (NIR) laser diodes. In the present embodiment, each laser assembly 140 includes two near-infrared laser diodes 152, 153. A first near-infrared laser diode 152 is configured to operate at a pulse frequency from about 9.5 MHz to about 10 MHz (as controlled by the controller 120). The first near-infrared laser diode 152 has an operational wavelength selected from a wavelength range of about 780 nm to about 810 nm.

There is also included a second near-infrared laser diode 153. The second near-infrared laser diode 153 has an operational wavelength selected from a range of about 904 nm to about 945 nm. The second near-infrared laser diode 153 is configured to operate at a pulse frequency from about 3 MHz to about 3.5 MHz as controlled by the controller 120.

Each laser assembly 140 also includes at least one mid-infrared (MIR) laser diode 154. The mid-infrared laser diode 154 is configured to operate at a pulse frequency from about 6 MHz to about 6.5 MHz as controlled by the controller 120. The mid-infrared laser diode 154 has an operational wavelength selected from the wavelength range of about 1200 nm to about 1550 nm.

Each laser assembly 140 further includes at least one far-infrared (FIR) laser diode 155. In the illustrated embodiment, the far-infrared laser diode 155 has an operational wavelength selected from the wavelength range of about 2900 nm to about 3200 nm. The far-infrared laser diode 155 is configured to operate at a pulse frequency from about 7 MHz to about 7.5 MHz, as controlled by the controller 120.

Each laser assembly 140 further includes one or more visible-range (VIS) laser diodes. By the present embodiment, the laser assembly 140 includes two VIS laser diodes 156, 157. A first visible laser diode 156 has an operational wavelength selected from the wavelength range of about 630 nm to 700 nm. As controlled by the controller 120, the first visible laser diode 156 is configured to operate at a pulse frequency from about 4 MHz to about 4.5 MHz. A second visible laser diode 157 has an operational wavelength selected from the wavelength range of about 570 nm to about 600 nm. As controlled by the controller 120, the second visible laser diode 157 is configured to operate at a pulse frequency from about 5 MHz to about 5.5 MHz.

As is mentioned above, the controller 120 is configured to selectively activate each of the laser diodes 152-157 according to instructions of the particular light production program saved to the controller 120. Generally, one laser diode 152-157 is activated at any given moment in the light production program, although the order, duration, and repetition of use of any given one of the laser diodes 152-157 varies in different light production programs. The controller 120, being in operative connection with the waveform electronics assembly 144 and the laser diodes 152-157, allows for rigorous control of the light produced, including control of the order, duration, fluence, and repetition each laser diode 152-157.

It is noted that while the laser diodes 152-157 described herein are listed in a particular order, the order of the laser diodes 152-157 does not correspond or correlate to any particular illumination or control sequence. It is also noted that the physical placement of any particular diode 152-157 is additionally not meant to infer any particular meaning or effect on the light production program.

With reference to FIG. 5, a method 300 for delivering light to the subject for non-invasive light delivery using the device 100, i.e. operating the device 100, is illustrated. The method 300 is executed by the controller 120, although it is contemplated that different portions of the method 300 could be implemented within different components of the device 100.

The method 300 begins, at step 310, with causing the waveform electronics assembly 144 to produce a square-wave signal. The square-wave signal is produced by the waveform generator 145, with the duty cycle being selected by the controller 120, based at least in part on the light production program.

In at least some embodiments, the method 300 could then include communicating to the FSC 147 to modulate the signal frequency and amplitude for light production by one of the laser diodes 152-157.

The method 300 then continues, at step 320, with selecting a first laser diode from the laser diodes 152-157. The first laser simply refers to a first one of the laser diodes 152-157 to be fired in any given implementation of the method 300, and does not refer to any order or position of the corresponding laser diode.

The method 300 continues, at step 330, with causing the first laser diode to produce light, also referred to as firing. The method 300 then continues, at step 340, with controlling the first laser diode to fire with a first MHz modulation. The modulation is based at least in part on the laser diode 152-157 chosen in the program. In some cases, the particular pulse rate could also depend on parameters of the given implementation of the light production program.

The method 300 subsequently continues, at step 350, with causing the first laser diode to cease producing light. By the present technology, only one of the laser diodes 152-157 fires at a given moment and thus operation of one of the laser diodes 152-157 is ended before beginning operation of another one of the laser diodes 152-157.

The method 300 continues, at step 360, with selecting a second laser diode from the laser diodes 152-157, the second laser diode being a different diodes then the first selected diode. Selection of the second laser diode is based, at least in part, on the particular of the light production program.

The method 300 continues, at step 370, with causing the second laser diode to produce light. The method 300 continues, at step 380, with controlling the second laser diode to fire with a second MHz modulation. Controlling the second laser diode to fire with the second MHz modulation includes modulating an input signal to the diode by the FSC 147. The modulation is based at least in part on the laser diode 152-157 chosen as the second laser diode in the light production program. In some cases, the particular pulse rate could also depend on parameters of the given implementation of the light production program.

The method 300 continues, at step 390, with causing the second laser to cease producing light. When the device 100 has completed the light production program, the controller 120 ceases operation of the laser diodes 152-157.

Depending on the particular light production program, according to which the controller 120 controls the laser diodes 152-157, the method 300 could include a plurality of steps of firing and ending firing of any and/or all of the laser diodes 152-157.

Depending on the particular light production program, the method 300 could include selectively activating each of the laser diodes 152-157. In at least some programs, in response to selecting one of the near-infrared laser diodes 152, 153, the method 300 could include causing the corresponding laser diode 152, 153 to operate at one of: a pulse frequency from about 3 MHz to about 3.5 MHz and a pulse frequency of about 9.5 MHz to about 10 MHz.

In at least some programs, in response to selecting the mid-infrared laser diode 154, the method 300 could include causing the mid-infrared laser diode 154 to operate at a pulse frequency from about 6 MHz to about 6.5 MHz.

In at least some programs, in response to selecting the far-infrared laser diode 155, the method 300 could include causing the far-infrared laser diode 155 to operate at a pulse frequency from about 7 MHz to about 7.5 MHz.

In at least some programs, in response to selecting one of the visible-range laser diodes 156, 157, the method 300 could include causing the visible-range laser diode 156, 157 to operate at one of: a pulse frequency from about 4 MHz to about 4.5 MHz and a pulse frequency from about 5 MHz to about 5.5 MHz.

While the firing of the laser diodes 152-157 are listed in a particular order herein, the actual operational order of use of any one or all of the laser diodes 152-157 is not meant to be so limited. Depending on the particular light production program saved to the controller 120, the order, duration, repetition, and fluence (also referred to as dose) of use of each laser diode 152-157 could vary.

While the above-described embodiments have been described and shown with reference to particular steps performed in a particular order, it will be understood that these steps may be combined, sub-divided, or re-ordered without departing from the teachings of the present technology. At least some of the steps may be executed in parallel or in series. Accordingly, the order and grouping of the steps is not a limitation of the present technology.

It should be expressly understood that not all technical effects mentioned herein need to be enjoyed in each and every embodiment of the present technology. Modifications and improvements to the above-described embodiments of the present technology may become apparent to those skilled in the art. The foregoing description is intended to be exemplary rather than limiting. The scope of the present technology is therefore intended to be limited solely by the scope of the appended claims.

What is claimed is:

1. A device for non-invasive light delivery to a subject, the device comprising:
   a housing;
   a power source disposed in the housing;
   a controller disposed in the housing, the controller being electrically connected to the power source;
   at least one waveform electronics assembly disposed in the housing, the at least one waveform electronics assembly being operatively connected to the power source and the controller;
   a plurality of laser diodes disposed in the housing, each of the plurality of laser diodes being operatively connected to the at least one waveform electronics assembly,
   the plurality of laser diodes being configured to operate in a super-pulsed regime, the controller being configured to operate the plurality of laser diodes with a Megahertz (MHz) modulation between about 3 MHz to about 10 MHz,
   the plurality of laser diodes comprising:
      at least one near-infrared laser diode,
      at least one mid-infrared laser diode,
      at least one far-infrared laser diode, and
      at least one visible-range laser diode,
   each of the plurality of laser diodes operating with a duty cycle of less than 50% and a pulse duration of on an order of nanoseconds,
   each of the plurality of laser diodes operating with a peak power in milliwatts range;
   a plurality of optical fibers comprising:
      at least one first fiber optically connected to the at least one near-infrared laser diode at a proximal end thereof,
      at least one second fiber optically connected to the at least one mid-infrared laser diode at a proximal end thereof,
      at least one third fiber optically connected to the at least one far-infrared laser diode at a proximal end thereof, and
      at least one fourth fiber optically connected to the at least one visible-range laser diode at a proximal end thereof,
   the plurality of optical fibers being bundled into at least one fiber bundle, the at least one fiber bundle extending from an interior of the housing to an exterior of the housing,
   a distal end of the at least one fiber bundle being arranged and configured for delivering light from the plurality of optical fibers to the subject, the distal end of the at least one fiber bundle being formed at least in part by a distal end of each of the plurality of optical fibers.

2. The device of claim 1, wherein:
   the controller comprises at least one storage media and at least one processor; and
   the at least one processor is configured to execute a light production program saved to the at least one storage media.

3. The device of claim 2, wherein the controller is configured to selectively and separably activate each of the plurality of laser diodes according to instructions of the light production program, the controller being configured to selectively activate and deactivate each of the plurality of laser diodes to provide various light-delivery patterns to the subject.

4. The device of claim 1, further comprising a communication assembly operatively connected to the controller, the communication assembly being configured to provide outward communication of information from the controller.

5. The device of claim 4, wherein the communication assembly is further configured to receive reprogramming instructions for the controller, the controller being selectively re-programmable when connected to a secure communication connection via the communication assembly.

6. The device of claim 1, wherein the at least one waveform electronics assembly comprises:
   at least one waveform generator;
   at least one frequency selector circuit operatively connected to the at least one waveform generator; and
   at least one buffering circuit operatively connected to the at least one frequency selector circuit.

7. The device of claim 1, wherein:
   the at least one waveform electronics assembly comprises a plurality of laser waveform assemblies;
   each assembly of the plurality of laser waveform assemblies is operatively connected to a corresponding one of the plurality of laser diodes; and
   each assembly of the plurality of laser waveform assemblies comprises;
      a waveform generator,
      a frequency selector circuit operatively connected to the waveform generator, and
      a buffering circuit operatively connected to the frequency selector circuit and the corresponding one of the plurality of laser diodes.

8. The device of claim 1, wherein the at least one near-infrared laser diode comprises:
   a first near-infrared laser diode configured to operate at a pulse frequency from about 9.5 MHz to about 10 MHz; and
   a second near-infrared laser diode configured to operate at a pulse frequency from about 3 MHz to about 3.5 MHz.

9. The device of claim 8, wherein the first near-infrared laser diode has an operational wavelength selected from a wavelength range of about 780 nm to about 810 nm.

10. The device of claim 8, wherein the second near-infrared laser diode has an operational wavelength selected from a wavelength range of about 904 nm to about 945 nm.

11. The device of claim 1, wherein the at least one mid-infrared laser diode is configured to operate at a pulse frequency from about 6 MHz to about 6.5 MHz.

12. The device of claim 11, wherein the at least one mid-infrared laser diode has an operational wavelength selected from a wavelength range of about 1200 to about 1550 nm.

13. The device of claim 1, wherein the at least one far-infrared laser diode is configured to operate at a pulse frequency from about 7 MHz to about 7.5 MHz.

14. The device of claim 13, wherein the at least one far-infrared laser diode has an operational wavelength selected from a wavelength range of about 2900 nm to about 3200 nm.

15. The device of claim 1, wherein the at least one visible-range laser diode comprises:
   a first visible laser diode configured to operate at a pulse frequency from about 4 MHz to about 4.5 MHz; and
   a second visible laser diode configured to operate at a pulse frequency from about 5 MHz to about 5.5 MHz.

16. The device of claim 15, wherein:

the first visible laser diode has an operational wavelength selected from a wavelength range of about 630 nm to 700 nm; and the second visible laser diode has an operational wavelength selected from a wavelength range of about 570 nm to about 600 nm.

17. The device of claim 1, further comprising:

at least one adhesive pad connected to the distal end of the at least one fiber bundle; and wherein:

when the at least one adhesive pad is applied to the subject, the at least one adhesive pad is configured to position the distal end of the at least one fiber bundle such that light from the plurality of laser diodes is delivered to the subject when the device is in use.

18. The device of claim 1, wherein:

the at least one waveform electronics assembly includes a plurality of waveform electronics assemblies;

the plurality of laser diodes includes a plurality of diode groups, each diode group of the plurality of diode groups comprising at least:

a first near-infrared laser diode, a second near-infrared laser diode, a mid-infrared laser diode, a far-infrared laser diode, a first visible-range laser diode, and a second visible-range laser diode, each diode group being operatively connected to a corresponding one of the plurality of waveform electronics assemblies;

the at least one fiber bundle including a plurality of fiber bundles; and each fiber bundle of the plurality of fiber being optically connected to a corresponding one of the plurality of diode groups.

19. A device for non-invasive delivery of complex light signals to a subject, the device comprising:

a housing;

a power source disposed in the housing;

a controller disposed in the housing, the controller being electrically connected to the power source;

at least one waveform electronics assembly disposed in the housing, the at least one waveform electronics assembly being operatively connected to the power source and the controller;

a plurality of laser diodes disposed in the housing, each of the plurality of laser diodes being operatively connected to the at least one waveform electronics assembly, the plurality of laser diodes being configured to operate in a super-pulsed regime, the controller being configured to operate the plurality of laser diodes with a Megahertz (MHz) modulation between about 3 MHz to about 10 MHz, the plurality of laser diodes comprising:

at least one first near-infrared laser diode, the at least one first near-infrared laser diode having an operational wavelength selected from a wavelength range of about 780 nm to about 810 nm, at least one second near-infrared laser diode, the at least one second near-infrared laser diode having an operational wavelength selected from a wavelength range of about 904 nm to about 945 nm, at least one mid-infrared laser diode, the at least one mid-infrared laser diode having an operational wavelength selected from a wavelength range of about 1200 to about 1550 nm, at least one far-infrared laser diode, the at least one far-infrared laser diode having an operational wavelength selected from a wavelength range of about 2900 nm to about 3200 nm, at least one first visible-range laser diode, the at least one first visible-range laser diode having an operational wavelength selected from a wavelength range of about 630 nm to 700 nm, and at least one second visible-range laser diode, the at least one second visible-range laser diode has an operational wavelength selected from a wavelength range of about 570 nm to about 600 nm, each of the plurality of laser diodes operating with a duty cycle of less than 50% and a pulse duration of on an order of nanoseconds, each of the plurality of laser diodes operating with a peak power in milliwatts range; and a plurality of optical fibers, each one of the plurality of optical fibers being operative connected to a corresponding one of the plurality of laser diodes, the plurality of optical fibers being bundled into at least one fiber bundle, the at least one fiber bundle extending from an interior of the housing to an exterior of the housing, a distal end of the at least one fiber bundle being arranged and configured for delivery of complex light signals from the plurality of optical fibers to the subject, the distal end of the at least one fiber bundle being formed at least in part by a distal end of each of the plurality of optical fibers.

* * * * *